(12) United States Patent
Lev et al.

(10) Patent No.: US 8,875,579 B2
(45) Date of Patent: Nov. 4, 2014

(54) METHOD AND APPARATUS FOR NON-DESTRUCTIVE WELD TESTING

(75) Inventors: Leonid C. Lev, West Bloomfield, MI (US); Randy Gu, Rochester Hills, MI (US); Lianxiang Yang, Rochester Hills, MI (US); Nan Xu, Auburn Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 275 days.

(21) Appl. No.: 13/429,496

(22) Filed: Mar. 26, 2012

(65) Prior Publication Data

US 2013/0247672 A1 Sep. 26, 2013

(51) Int. Cl.
*G01M 7/02* (2006.01)

(52) U.S. Cl.
USPC ............................................................ 73/588

(58) Field of Classification Search
USPC ........... 73/588, 599–644, 649–657, 842, 827, 73/788, 818, 579
See application file for complete search history.

(56) References Cited

U.S. PATENT DOCUMENTS

| | | | |
|---|---|---|---|
| 3,649,127 A * | 3/1972 | Kersch et al. | 356/458 |
| 4,139,302 A | 2/1979 | Hung et al. | |
| 4,408,881 A | 10/1983 | Clarady, Jr. et al. | |
| 5,146,289 A | 9/1992 | Newman | |
| 6,040,900 A | 3/2000 | Chen | |
| 6,043,870 A | 3/2000 | Chen | |
| 6,175,411 B1 | 1/2001 | Telschow et al. | |
| 6,717,681 B1 | 4/2004 | Bard et al. | |
| 2003/0079552 A1 * | 5/2003 | Bossi et al. | 73/827 |
| 2004/0165176 A1 | 8/2004 | Bard et al. | |
| 2005/0279172 A1 | 12/2005 | Schreier et al. | |
| 2008/0237366 A1 * | 10/2008 | Ehlert et al. | 239/102.2 |
| 2010/0019153 A1 | 1/2010 | Zalameda et al. | |
| 2010/0162825 A1 | 7/2010 | Karp et al. | |
| 2011/0020694 A1 * | 1/2011 | Khakhalev et al. | 429/158 |
| 2011/0079088 A1 * | 4/2011 | Peecock et al. | 73/827 |
| 2012/0101191 A1 * | 4/2012 | Enomoto et al. | 523/466 |

FOREIGN PATENT DOCUMENTS

| | | | |
|---|---|---|---|
| DE | 10010791 A1 | 9/2001 | |
| DE | 10217183 A1 | 10/2003 | |
| DE | 102008041904 | * 3/2010 | B41F 33/14 |

* cited by examiner

*Primary Examiner* — Peter Macchiarolo
*Assistant Examiner* — Anthony W Megna Fuentes

(57) ABSTRACT

A method for detecting the integrity of a bond of a multi-piece work piece includes capturing a first image of the work piece, stressing the work piece, capturing a stressed image of the work piece, and comparing the first image of the work piece with the stressed image of the work piece to determine the integrity of the bond.

18 Claims, 6 Drawing Sheets

US 8,875,579 B2

METHOD AND APPARATUS FOR NON-DESTRUCTIVE WELD TESTING

TECHNICAL FIELD

This disclosure is related to non-destructively testing weld coalescence.

BACKGROUND

The statements in this section merely provide background information related to the present disclosure and may not constitute prior art.

Bonding is a method of joining two materials together to form a single contiguous material into a work piece. The bonding process can include adhering, welding, and crimping. The two materials can be like materials, i.e., metals combined together or plastics combined together, or dissimilar materials, i.e., a combination of dissimilar metals or combination of metals and plastics. In the case of welding, the two materials are typically of similar chemical composition, e.g., each composed of a ferrous or nonferrous metals, or can be differing chemical composition, e.g., combining ferrous and nonferrous metals. The welding processes can include many forms, including arc welding, oxyfuel welding, resistance welding, electroslag welding, laser beam welding, ultrasonic welding, and electron beam welding.

Welding can be localized or run the length of the interaction of the work piece. Examples of localized welding are spot welding and projection welding. Spot welding is typically a form of resistance welding wherein two electrodes hold the work pieces together and current is run through the electrodes to form a weld nugget. Projection welding utilizes raised sections on one or both of the materials to be joined. Heat can be applied to the raised sections creating a weld nugget at the projections.

The welding process has many variables to consider including the duration and the amount of energy used. Once these have been determined, the welding process may be consistently repeated. Variation in either the duration or the amount of energy supplied can cause weak weld integrity or no weld integrity when an incomplete or no weld is formed in the work piece. The incomplete or no weld having weak integrity or no integrity results in less than desired joint properties, e.g., strength and electrical transfer, and can cause unexpected performance of the work piece.

SUMMARY

A method for detecting the integrity of a bond of a multi-piece work piece includes capturing a first image of the work piece, stressing the work piece, capturing a stressed image of the work piece, and comparing the first image of the work piece with the stressed image of the work piece to determine the integrity of the bond.

BRIEF DESCRIPTION OF THE DRAWINGS

One or more embodiments will now be described, by way of example, with reference to the accompanying drawings, in which:

FIGS. 4-1, 4-2, and 4-3 are schematic illustrations of shearography results during vibrational loading of a work piece with three good spot welds at different vibrational frequencies, 4.5 KHz, 9.3 KHz, and 11.5 KHz, respectively, in accordance with the present disclosure; and FIGS. 5-1, 5-2, and 5-3 are schematic illustrations of shearography results during vibrational loading of a work piece with single good spot weld at different vibrational frequencies, 5.0 KHz, 8.7 KHz, and 11.9 KHz, respectively, in accordance with the present disclosure.

DETAILED DESCRIPTION

Figure 1:
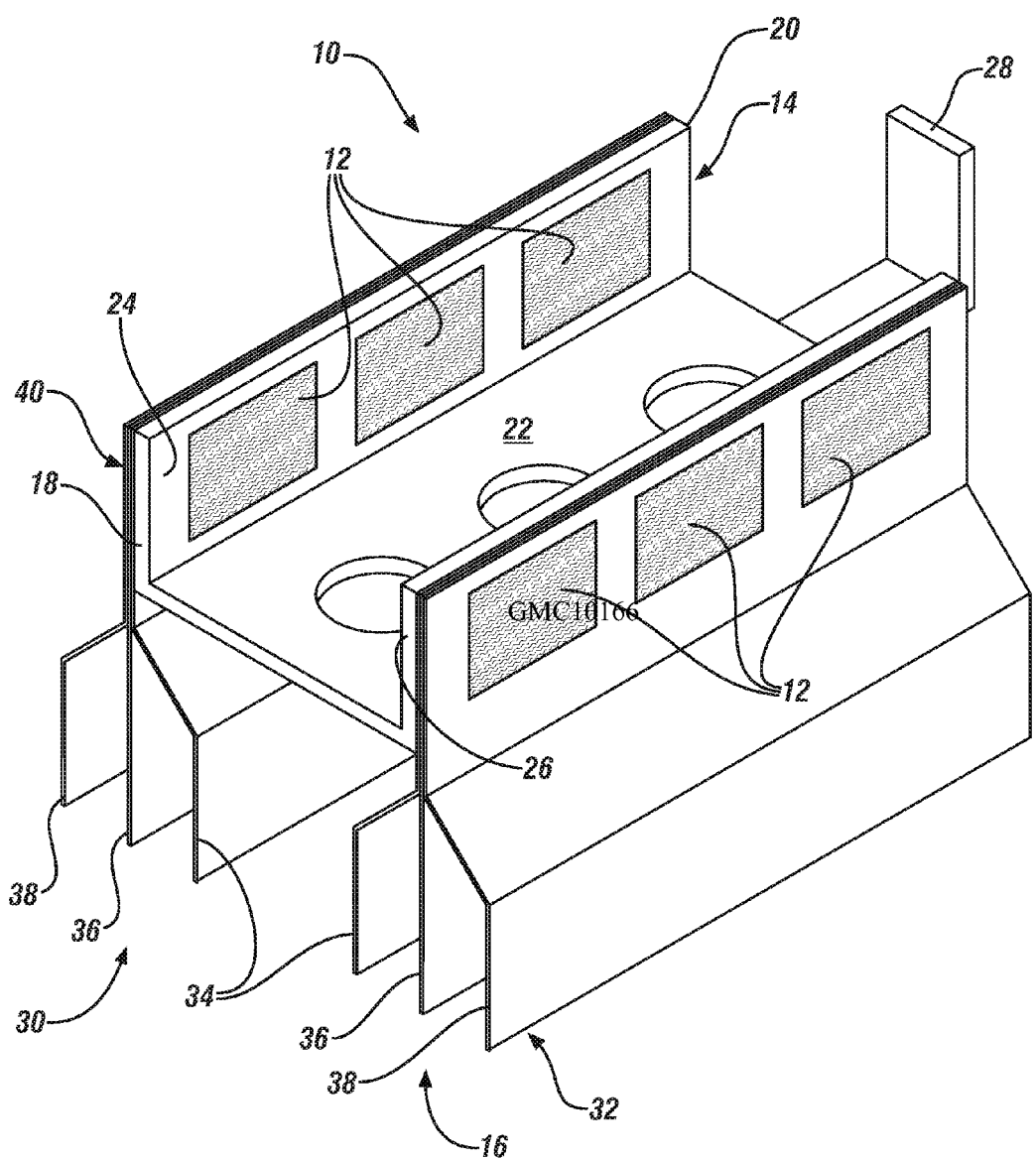
FIG. 1 schematically illustrates an exemplary intercell connector that includes a plurality of welds for use in a battery, in accordance with the disclosure.

Referring now to the drawings, wherein the showings are for the purpose of illustrating certain exemplary embodiments only and not for the purpose of limiting the same, FIG. 1 schematically illustrates an exemplary intercell connector 10 that includes a plurality of bonds, i.e., spot welds 12, for use in a battery. The intercell connector 10 includes a connector bus 14 for interconnecting a plurality of plates 16. The connector bus 14 has a generally U-shaped cross section that extends from a first end 18 to a distal second end 20. The U-shaped cross section includes a base 22 and first and second attachment members 24 and 26, respectively. The second end 20 includes an interconnection tab 28 for interconnecting the battery to other batteries and devices as is required for a specific application.

The first and second attachment members 24, 26 are welded to a respective first and second sets of plurality of plates 30, 32. The first and second sets of plurality of plates 30, 32 includes an inner plate 34, a middle plate 36, and an outer plate 38. Since the first and second sets of plurality of plates 30, 32 iares identical, only the first set of plurality of plates 30 will be described in detail. The inner plate 34, middle plate 36, and outer plate 38 include a vertical section 40 that generally overlap the vertical attachment member 24 for bonding thereto. In the exemplary embodiment the bonding is achieved by three spot welds 12 securing the first set of plurality of plates 30 to the connector bus 14. The inner plate 34 extends below the base 22, steps inwardly toward a center of the base 22, then downwardly in a generally vertical direction away from the base 22 to a bottom edge 42. The middle plate 36 extends generally vertically downward to a bottom edge 44 in line with the bottom edge 42. The outer plate 38 is symmetrically opposite of the inner plate 34 about the middle plate 36, i.e., the step is outwardly away from the center of the base 22 and has a bottom edge 46 in line with bottom edge 42. The inner plate 34, middle plate 36, and outer plate 38 can then be inserted into an electrolyte reservoir thereby creating a chemical reaction to produce electricity. It will be apparent that the first and second set of plurality of plates 30, 32 can be a plurality of pasted plates, Planté plates, flat plates, tubular plates, or any other electrode capable of transferring electricity when introduced into an electrolyte.

Each spot weld 12 fuses the inner plate 34, middle plate 36, and outer plate 38 to the connector bus 14 and permits efficient current flow from each of the inner, middle, and outer plates 34, 36, 38 to the connector bus 14. The connector bus 14 transfers the current flow to the other batteries or devices that are connected therewith. An inadequate spot weld 12 that does not properly fuse a single plate to the remainder of the plurality of plates 30, 32 and to the connector bus 14 creates sub-optimum current flow and can prevent current flow altogether. The inadequate spot weld 12 can prevent the battery from providing the expected amount of current thereby preventing proper operation of a device that is being supplied current. The inadequate spot weld 12 can be determined by utilizing shearography.

Figure 2:
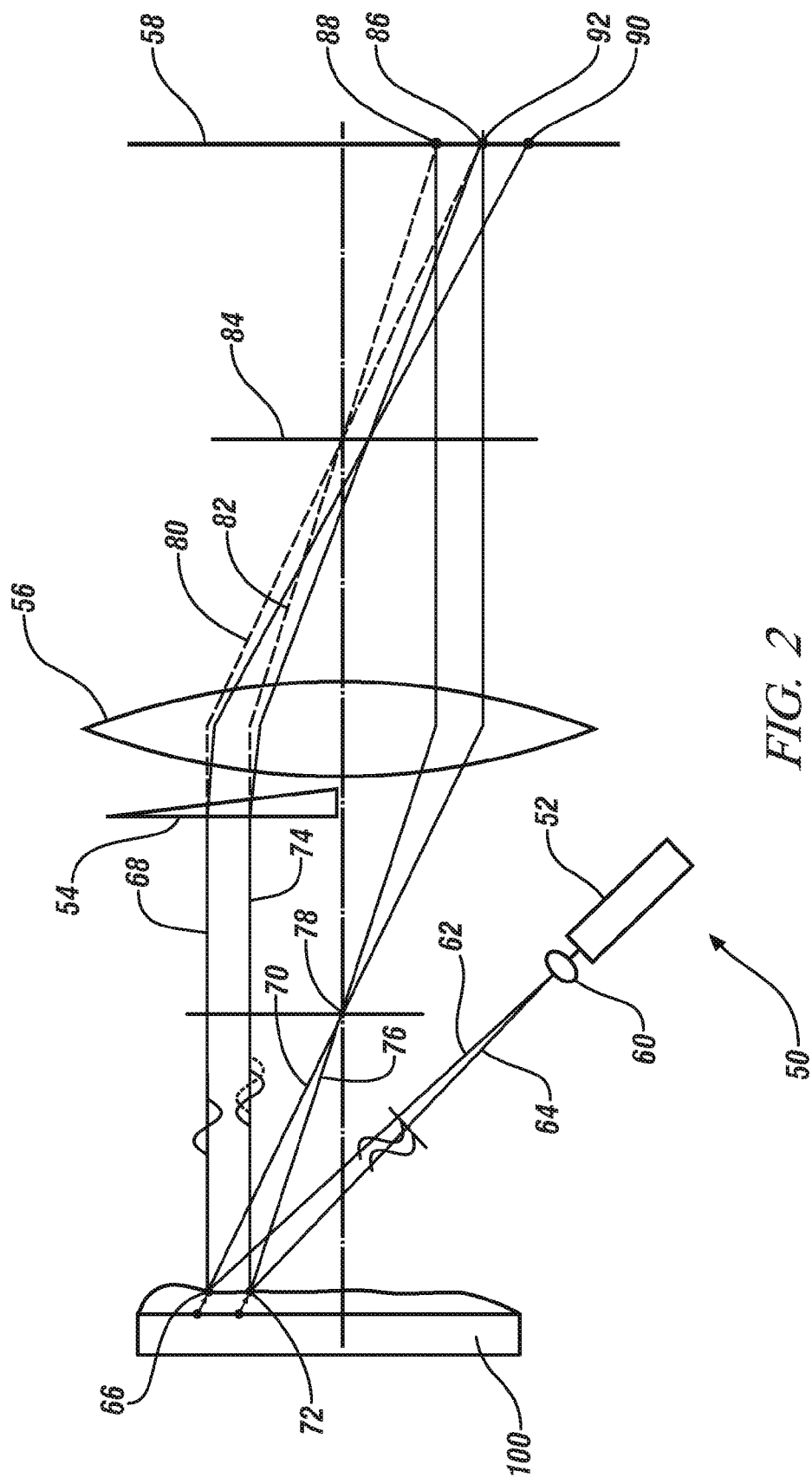
FIG. 2 is a schematic illustration of a shearography testing apparatus in use on a work piece, in accordance with the present disclosure.

FIG. 2 is a schematic illustration of a shearography testing apparatus 50 for use on a work piece 100, e.g., the intercell connector 10. The shearography testing apparatus 50 includes a laser 52, wedge 54, lens 56, and image capturing device 58. The laser 52 is a light emitting device that can be precisely aimed to illuminate specific areas of a target or the entire target, e.g., the work piece 100. The wedge 54 is capable of changing the trajectory of the light source by a predetermined amount. The lens 56 receives divergent light emissions and refocuses the light emissions at a predetermined distance thereby maintaining a scaled image. The image capturing device 58 is a digital image capturing sensor, such as a CCD sensor as is commonly known in the art, capable of recording an image projected upon the sensor. The lens 56 is located between the work piece 100 and the image capturing device 58 at a predetermined distance to refocus the light emissions in accordance with the shearography testing apparatus 50. The wedge 54 is located between the work piece 100 and the lens 56 and is positioned over one-half of the lens 56 to create an appropriate change in light trajectory for one-half of the light entering the lens 56.

The work piece 100 is positioned within the shearography testing apparatus 50 in a way that allows the laser 52 to illuminate the work piece 100. The light from the laser 52 can be projected on to the work piece 100 through a beam splitter 60. The beam splitter 60 spreads the light from the laser 52 over a wider area than the original light beam, represented by a first beam 62 and a second beam 64. It is understood that discussion of the first beam 62 and second beam 64 is only for easily defined reference points and that the portion in between the first beam 62 and second beam 64 behaves similarly to the closest reference beam.

The first beam 62 illuminates a first point 66 on the work piece 100 that is refracted toward the lens 56 in a first upper beam 68 and first lower beam 70. The second beam 64 illuminates a second point 72 on the work piece 100 that is refracted toward the lens 56 in a second upper beam 74 and a second lower beam 76. The first lower beam 70 and second lower beam 76 enter the lens 56 and are projected onto the image capturing device 58 at a first projected point 86 and a second projected point 88.

The first upper beam 68 and second upper beam 74 are projected to the wedge 54. The wedge 54 refracts a majority of the first upper beam 68 and second upper beam 74 thereby creating an offset of a predetermined amount. The portion of light that is not offset is shown by a first focus beam 80 and a second focus beam 82. A first image is presented to the image capturing device 58 as indicated by the first projected point 86 and the second projected point 88 representing the area of the work piece 100 between the first point 66 and the second point 72. The first upper beam 68 and the second upper beam 74 has a focal point along line 84 at the same distance between the lens 56 and image capturing device 58 as the first focus beam 80 and the second focus beam 82. A second image is presented to the image capturing device 58 as indicated by an offset first projection point 90 and an offset second projection point 92, the latter corresponding to the position of the first projected point 86.

The resulting first and second images provide a superimposed first image on the image capturing device 58 that is recorded. The work piece 100 is subjected to stress, e.g., changes in loading, temperature, vacuum, and vibration, then a superimposed stressed image is recorded from the image capturing device 58. The first image and the stressed image are compared, i.e., added or subtracted, to determine shear lines and impurities in the work piece 100 to create a shear image. The shear image may be compared to a reference image that indicates an expected resultant image. The comparison can be completed either manually or by way of automation. It is evident that when the work piece 100 is subjected to a vibrational load, the images can be recorded at the extremes of excitation of the work piece 100, i.e., at a position closest to and furthest from the image capturing device 58.

Figure 3:
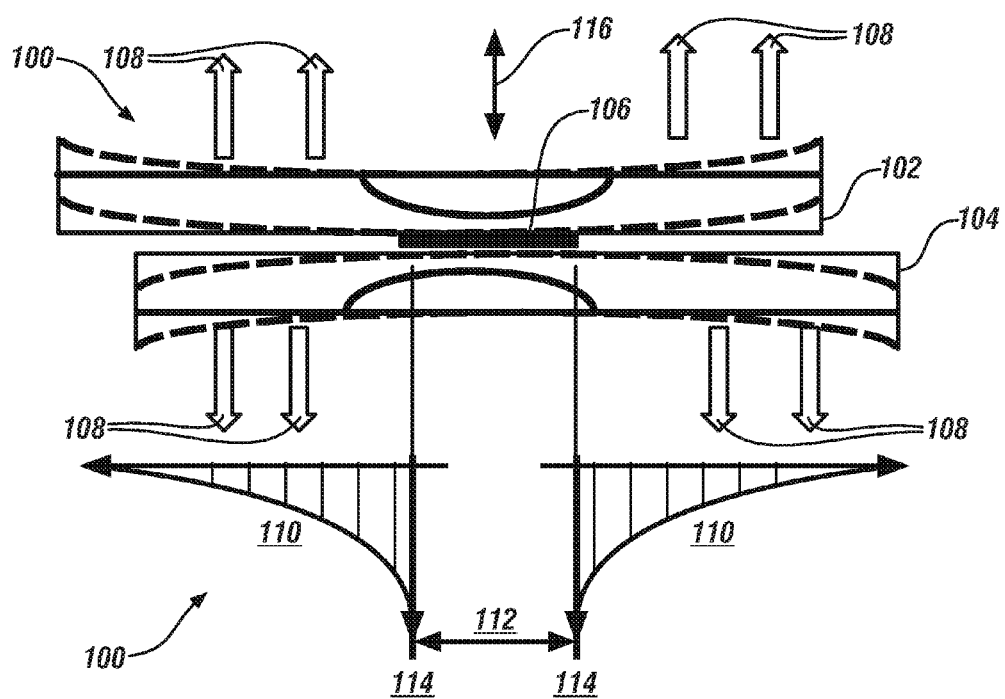
FIG. 3 is a schematic illustration of an exemplary work piece having a bonded area and a free area with a representative shear diagram during loading, in accordance with the disclosure.

FIG. 3 is a schematic illustration of an exemplary work piece 100 having a bonded area, such as a weld, and a free area, an area without any bonding, with a representative shear diagram under loading. The work piece 100 includes an upper member 102 and an adjacent lower member 104 that have a single common bonded area, i.e., spot weld 106. The load is applied equally to the work piece 100 along the upper and lower members 102, 104 in a direction away from the spot weld 106, i.e., in the direction represented by arrows 108. The spot weld 106 maintains the relationship between the upper and lower members 102, 104 whereas deflection increases as the distance increases from the spot weld, as indicated by the dashed lines. The strain diagram 110 indicates an area of no strain 112 corresponding to the size of the spot weld 106. However, a relatively large strain 114 exists adjacent the spot weld 106 and decreases as the distance from the spot weld 106 increases.

A vibrational load 116 may be applied to the work piece. The vibrational load 116 can be randomly applied or controlled to a specific frequency or series of frequencies. The vibrational load 116 results in a similar occurrence as discussed above with relation to the load. That is, as the work piece 100 is excited, the point at which the work piece 100 is bonded, i.e., spot welded 106, and maintains the relationship between the upper and lower members 102, 104. Deflection of the upper and lower members 102, 104 increases as the distance increases from the spot weld, as indicated by the dashed lines. The strain diagram 110 remains the same, i.e., the area of no strain 112 corresponds to the size of the spot weld 106 and a relatively large strain 114 adjacent the spot weld 106 that decreases as the distance from the spot weld 106 increases. This relationship holds for a single spot weld 106 or a series of spot welds. The frequency of the vibrational load 116 can be changed to match the spacing of the spot welds in such a way as to provide easily distinguishable shearography results. It will be apparent that the vibrational load 116 can be at the natural frequency of the work piece or one or more pieces that form the work piece.

The shearography is able to detect the strain 114 adjacent the spot welds 106 by creating a node point at the location of the spot weld 106, i.e., the spot welds 106 will show a consistently shaded image during the shearography image comparison. Where a spot weld 106 has weak weld integrity or no weld integrity, the shearography image will show part deflection by way of shaded variation through the portion of the spot weld that has weak or no weld integrity.

Figures 1, 4:
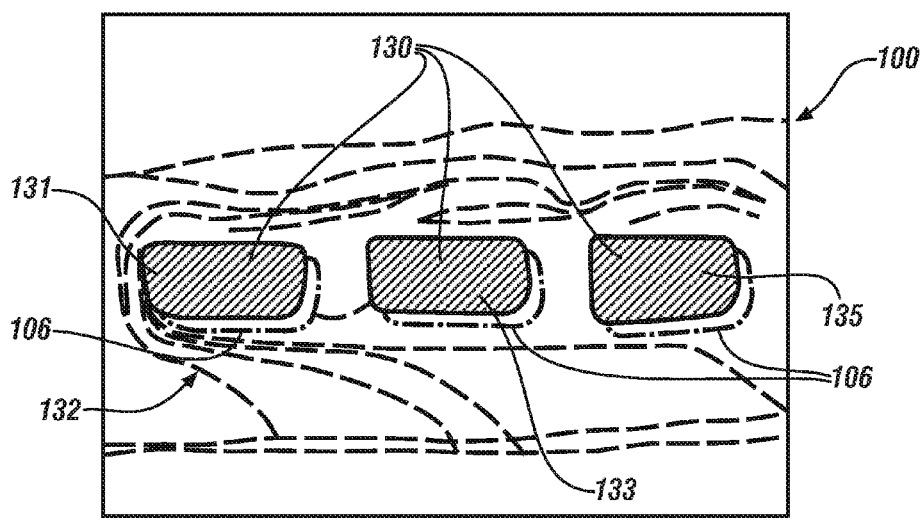
Figures 2, 4:
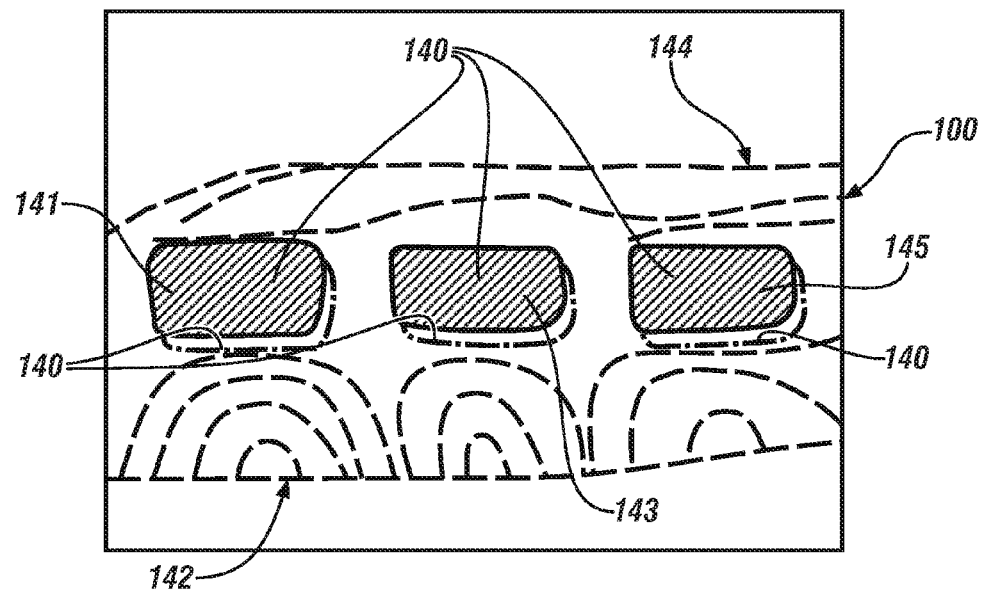
Figures 3, 4:
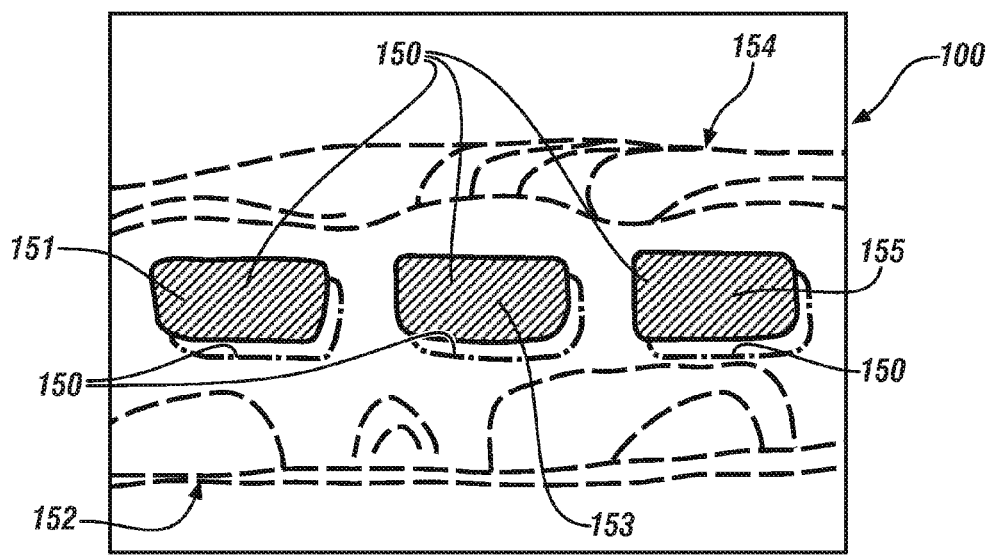

FIGS. 4-1, 4-2, and 4-3 are schematic illustrations of shearography during vibrational loading of a work piece with three good spot welds at different vibrational frequencies, 4.5 KHz, 9.3 KHz, and 11.5 KHz, respectively. FIG. 4-1 is illustrative of the work piece 100 excited to a vibrational frequency of 4.5 KHz and displaying three node points 130, a left node point 131, a middle node point 133, and a right node point 135, indicating three spot welds. The node points 130 indicate well formed spot welds, i.e., the respective node points 130 are consistent with the overall shape of the spot weld. A double image of the left, middle, and right node points 131, 133, 135 occur due to the shearography images taken at the extremes of the vibration cycle, i.e., the furthest point from the camera and the closest point to the image capturing device, being overlaid upon each other, as described above. Shear lines 132 occur at the 4.5 KHz frequency that wrap around the combination of the three node points 130. The shear lines 132 begin generally under the middle and left node points 133, 131, respectively, at the edge of the work piece and extend upwardly toward the associated node point 130 and to the left. The shear lines 132 extend around and above the left node point 131. The shear lines 132 continue by extending to the right node point with a generally upwardly trend. Additional shear lines begin at the top of the middle and right node points and follow the same general pattern.

FIG. 4-2 is illustrative of the work piece 100 excited to a vibrational frequency of 9.3 KHz and displaying three node points 140, a left node 141, a middle node 143, and a right node 145, indicating three spot welds. Each of the node points 140 show well formed spot welds. The double image of the node points 140 occur due to the shearography images taken at the extremes of the vibration cycle, as discussed above. Due to the higher frequency with respect to FIG. 4-1, the lower shear lines 142 occur along the bottom of each of the node points 140 in a generally half elliptical pattern with a closed end in line with the respective node point 140 and an open end extending to the end of the work piece. Since each of the left node 141, the middle node 143, and the right node 145 have associated lower shear lines 142, the lower shear lines 142 help identify when spot weld is well formed. The upper shear lines 144 start above each of the node points 140 extend upwardly and turn to the right in a generally horizontal direction.

FIG. 4-3 is illustrative of the work piece 100 excited to a vibrational frequency of 11.5 KHz and displaying three node points 150, a left node 151, a middle node 153, and a right node 155, indicating three spot welds. Each of the node points 150 show three well formed spot welds. The double image of the node points 150 occurs due to the shearography images taken at the extremes of the vibration cycle, as discussed above. Due to the higher frequency with respect to FIGS. 4-1 and 4-2, the lower shear lines 152 along the bottom of the node points 150 behave differently. The lower shear lines 152 have three groupings, each with a generally half-elliptical pattern with a closed end toward the node point 150, however only the left set of lower shear lines 152 remains directly under the left node point 151. The middle set of lower shear lines 152 is offset from the middle node point 153 and generally aligned under a left side of the middle node point 153. The right set of lower shear lines 152 is formed under the right node point 155 but further extends under a right portion of the middle node point 153. The upper shear lines 154 are generally centered above each of the node points 150 extending upwardly then turning right to a generally horizontal direction.

Figures 1, 5:
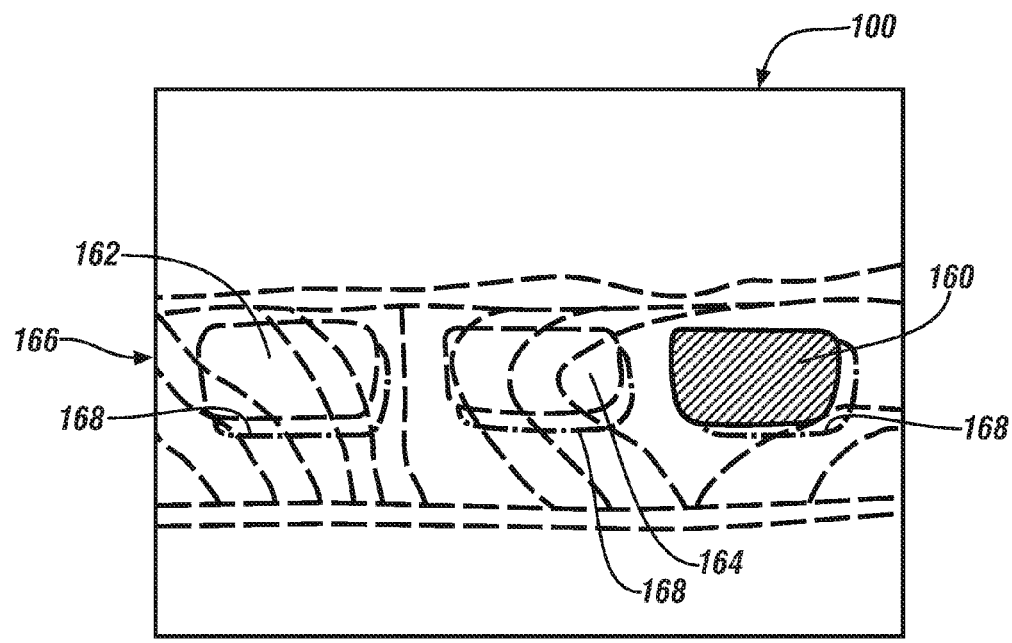
Figures 2, 5:
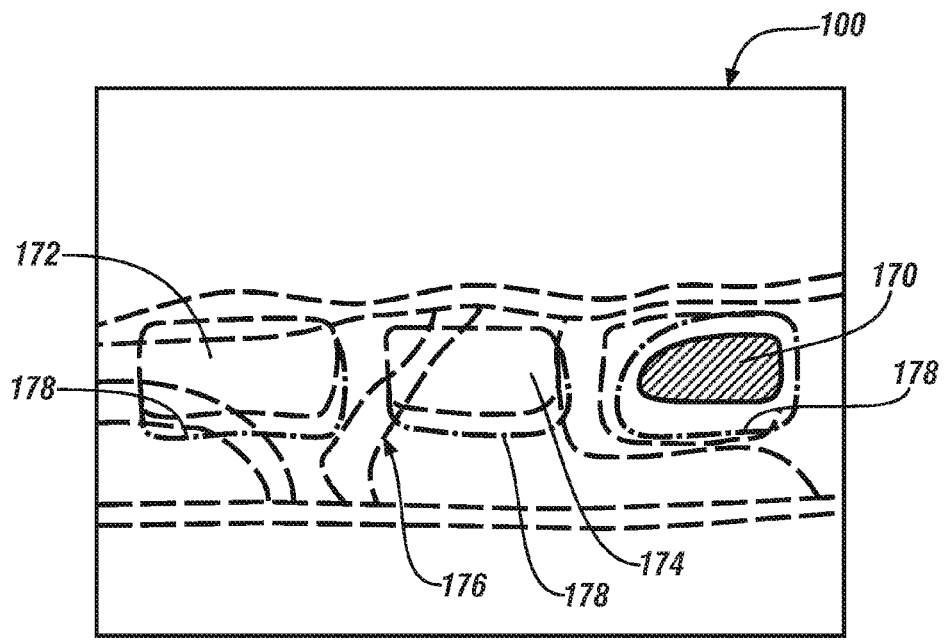
Figures 3, 5:
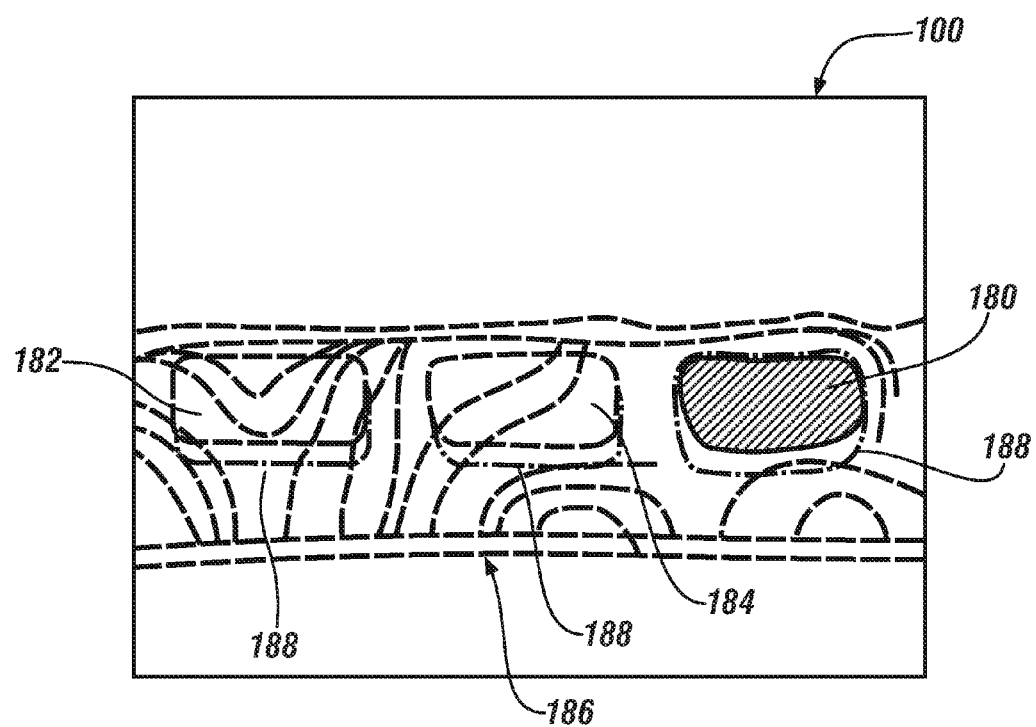

FIGS. 5-1, 5-2, and 5-3 are schematic illustrations of shearography during vibrational loading of a work piece with single good spot weld at different vibrational frequencies, 5.0 KHz, 8.7 KHz, and 11.9 KHz, respectively. FIG. 5-1 is illustrative of the work piece 100 excited to a vibrational frequency of 5.0 KHz and displaying a single node point 160 indicating one well formed spot weld and a left and middle indentation 162, 164 at areas spot welds failed to form. A double image of the node point 160 and the left and middle indentations 162, 164 occur due to the shearography images taken at the extremes of the vibration cycle, i.e., the furthest point from the camera and the closest point to the camera, being overlaid upon each other. Shear lines 166 surround the right node point 160 due to the stability of the spot weld. Both the left and middle indentations 162, 164 include a series of shear lines 166 that extend through the left and middle indentations 162, 164. The shear lines 166 extending through the left and middle indentations 162, 164 is indicative of a failed spot weld in each of the left and middle indentation locations 162, 164.

FIG. 5-2 is illustrative of the work piece 100 excited to a vibrational frequency of 8.7 KHz and displaying a single node point 170 and a left and middle indentation 172, 174, respectively at areas spot welds failed to form. A double image of the node point 170 and the left and middle indentations 172, 174 occur due to the shearography images taken at the extremes of the vibration cycle, as discussed above. The left and middle indentations 172, 174 are indicative of failed spot weld locations. Shear lines 176 surround the right node point 170 due to the stability of the spot weld. The shearography image of the node point 170 is smaller than the respective indentation representing a smaller than expected weld joint indicating weak weld integrity. Both the left and the middle indentations 172, 174 include a series of shear lines 176 that extend through the left and middle indentations 172, 174 and represent failed spot welds at the left and middle indentation locations.

FIG. 5-3 is illustrative of the work piece 100 excited to a vibrational frequency of 11.9 KHz and displaying a single node point 180 and a left and middle indentation 182, 184, respectively, at areas spot welds failed to form. A double image of the node point 180 and the left and middle indentations 182, 184 occur due to the shearography images taken at the extremes of the vibration cycle, as discussed above. Shear lines 186 surround the right node point 180 due to the stability of the spot weld. The right node point 180 is approximately the same shape as the respective indentation indicating a well formed spot weld. Both the left and middle indentations 182, 184 have a series of shear lines 186 extending through the left and middle indentations 182, 184 representing failed spot welds at each of the left and middle indentation locations.

The above description provides information upon which a non-destructive bond detection scheme can be assembled when stressing the work piece and capturing of stressed and non-stressed images or stressed images captured during extremes of excitation. One example can be providing a single frequency that is predicted to provide shear lines for shearographic imaging through non-bonded sections to detect proper bonding. Another example can be matching the vibrational frequency with the natural frequency of the bonded or non-bonded work piece for shearographic imaging to detect proper bonding. Still another example can be providing a series of frequencies for shearographic imaging to detect proper bonding. Yet another example is to capture a non-stressed image and stress the work piece via loading. In any case, a series of look-up tables or charts can be used to easily identify acceptable spot weld integrity with analysis occurring manually or through automation. Additionally, an area calculation can be used to determine if an appropriate amount of bonding has occurred for each bonding location of a work piece.

The disclosure has described certain preferred embodiments and modifications thereto. Further modifications and alterations may occur to others upon reading and understanding the specification. Therefore, it is intended that the disclosure not be limited to the particular embodiment(s) disclosed as the best mode contemplated for carrying out this disclo-

The invention claimed is:

1. Method for detecting the integrity of a bond of a multi-piece work piece, comprising:
   capturing a first image of the work piece;
   stressing the work piece;
   capturing a stressed image of the work piece;
   comparing the first image of the work piece with the stressed image of the work piece to identify shear lines indicative of strain in the work piece during the stressing;
   creating a shear image of the work piece based on the shear lines, the shear image including a node point indicating a location of the bond;
   comparing the shear image of the work piece to a reference image; and
   determining the integrity of the bond based on characteristics of the determined shear lines and the node point in relation to the reference image.

2. The method of claim 1, wherein stressing the work piece includes exciting the work piece to a specific frequency.

3. The method of claim 2, wherein capturing the first image of the work piece occurs at one extreme of the specific frequency and capturing the stressed image of the work piece occurs at the opposing extreme of the specific frequency.

4. The method of claim 2, wherein exciting the work piece to a specific frequency includes exciting the work piece to a series of specific frequencies.

5. The method of claim 4, wherein exciting the work piece to a series of specific frequencies includes exciting the work piece to a series of natural frequencies.

6. The method of claim 2, wherein exciting the work piece to a specific frequency includes exciting the work piece to the natural frequency of the work piece.

7. The method of claim 1, wherein stressing the work piece includes applying a compressive force to the work piece.

8. The method of claim 1, wherein stressing the work piece includes applying a tensile force to the work piece.

9. The method of claim 1, wherein comparing the shear image of the work piece to a reference image includes automating the comparing of the shear image and the reference image.

10. The method of claim 1, wherein comparing the image of the work piece with the stressed image of the work piece to determine to determine shear lines indicative of strain in the work piece during the stressing includes calculating the area of the bond.

11. The method of claim 1, wherein the work piece comprises a multi-piece battery terminal.

12. The method of claim 1, wherein the bond comprises a weld.

13. Method for detecting the bond of a multi-piece work piece, comprising:
    capturing a first image of the work piece;
    vibrating the work piece;
    capturing a stressed image of the work piece;
    comparing the first image to the stressed image to identify shear lines indicative of strain in the work piece during the vibrating; and
    creating a shear image of the work piece based on the shear lines, the shear image including a node point indicating a location of the bond.

14. The method of claim 13, wherein vibrating the work piece includes vibrating the work piece to a series of frequencies.

15. The method of claim 13, wherein vibrating the work piece includes vibrating the work piece to a series of pre-defined frequencies.

16. The method of claim 13, further comprising comparing the shear image to a reference image to detect the bond of the multi-piece work piece.

17. The method of claim 16, wherein comparing the shear image to the reference image includes calculating an area of the bond.

18. The method of claim 13, wherein the bond comprises an adhesive.

* * * * *